(12) United States Patent
Solinsky

(10) Patent No.: US 7,610,166 B1
(45) Date of Patent: Oct. 27, 2009

(54) GEOLOCATION SYSTEM AND METHOD FOR DETERMINING MAMMAL LOCOMOTION MOVEMENT

(75) Inventor: James Solinsky, 97 Roads End La., Severna Park, MD (US) 21146

(73) Assignee: James Solinsky, Serverna Park, MD (US)

( * ) Notice: Subject to any disclaimer, the term of this patent is extended or adjusted under 35 U.S.C. 154(b) by 146 days.

(21) Appl. No.: 11/878,319

(22) Filed: Jul. 23, 2007

Related U.S. Application Data

(60) Provisional application No. 60/832,129, filed on Jul. 21, 2006.

(51) Int. Cl.
G01B 5/02 (2006.01)
G01B 5/14 (2006.01)
G01B 7/02 (2006.01)

(52) U.S. Cl. .................. 702/160; 702/141; 702/142; 702/145; 702/146; 702/150; 702/151; 73/488; 73/489; 73/490; 73/493; 73/510

(58) Field of Classification Search ......... 702/141–142, 702/145–146, 150–151, 160; 73/488–490, 73/493, 510; 235/105
See application file for complete search history.

(56) References Cited

U.S. PATENT DOCUMENTS

| | | | |
|---|---|---|---|
| 5,406,845 A * | 4/1995 | Berger et al. | 73/379.09 |
| 5,583,776 A | 12/1996 | Levi et al. | |
| 5,724,265 A | 3/1998 | Hutchings | |
| 5,899,963 A | 5/1999 | Hutchings | |
| 6,122,960 A | 9/2000 | Hutchings et al. | |
| 6,292,106 B1 | 9/2001 | Solinsky et al. | |
| 6,305,221 B1 | 10/2001 | Hutchings | |
| 6,522,266 B1 | 2/2003 | Soehren et al. | |
| 6,579,097 B1 | 6/2003 | Sampson et al. | |
| 6,608,589 B1 | 8/2003 | Devereux et al. | |
| 6,706,003 B2 * | 3/2004 | Perrad et al. | 600/587 |
| 6,813,582 B2 | 11/2004 | Levi et al. | |
| 6,842,991 B2 | 1/2005 | Levi et al. | |
| 6,859,170 B2 | 2/2005 | Devereux et al. | |

OTHER PUBLICATIONS

Mulder, Axel. "Human Movement Tracking Technology," 1994, Simon Fraser University.*

Jerzy Wtorek et al. "Multifrequency Impedance Plethysmograph"; IEEE Instrumentation and Measurement Technology Conference; Jun. 4-6, 1996; pp. 1452-1455.

(Continued)

*Primary Examiner*—Tung S Lau
*Assistant Examiner*—Sujoy K Kundu
(74) *Attorney, Agent, or Firm*—Nixon & Vanderhye, PC

(57) ABSTRACT

An example geolocation system for mounting on a mammal incorporates simple sensing sleeves on the calves of the body support members, combined with an accelerometer based gravity direction and force sensing at the center of mass of the body. The example system is connected to a digital processing unit and a battery power supply to integrate the sensing to determine kinetic and potential energy of the body locomotion over time in a method that integrates out the aperiodic motion of the body about the center of mass, and uses the residual motion to measure the center of mass locomotion from a known point.

4 Claims, 8 Drawing Sheets
(6 of 8 Drawing Sheet(s) Filed in Color)

OTHER PUBLICATIONS

Svein I. Sagatun et al.; "Lagrangian Formulation Of Underwater Vehicles' Dynamics"; IEEE ISSN # 0-7803-0233 Aug. 1991; pp. 1029-1034.

Javier Rosell et al. "Reduction of Motion Artifacts Using a Two-Frequency Impedance Plethysmograph and Adaptive Filtering"; IEE Transactions on Biomedical Engineering, vol. 42, No. 10, Oct. 1995; pp. 1044-1048.

Kenji Ikeda et al.; "Improvement of Photo-Electric Plethysmograph Applying Newly Developed Opto-Electronic Devices"; IEEE Tencon 1999; pp. 1109-1112.

D. Eugene Hokanson et al. "An Electrically Calibrated Plethysmograph for Direct Measurement of Limb Blood Flow"; IEEE Transactions on Biomedical Engineering, vol. BME-22, No. 1, Jan. 1975; pp. 25-29.

M.D. Gldman et al. "Whole-body Plethysmography"; ERS Journals Ltd. 2005; pp. 15-43.

P.J. Pretorius et al. "The Use Of A Continuous Non-Invasive Blood Pressure Recorder to Study Experimental Stressors"; Noninvasive Cardiovascular DJTUI-CS IEEE Engineering in Medicine & Biology Society 11th Annual International Conference, 1989; pp. 128-129.

Alessio Urso et al. "Design of A High Signal to Ratio Electrical Impedance Plethysmograph"; IEEE Proceedings—1990 Southeastcon; pp. 1100-1104.

G. Lachapelle et al.; "Performance of Integrated HSGPS-IMU Technology for Pedestrian Navigation under Signal Masking"; ENC 2006, Manchester, May 8-10, 2006; pp. 1-24.

Altendorfer et al.; "Towards a Factored Analysis of Legged Locomotion Models"; Proceedings of the 2003 IEEE International Conference on Robotics and Automation Taipel, Taiwan, Sep. 14-19, 2003.

* cited by examiner

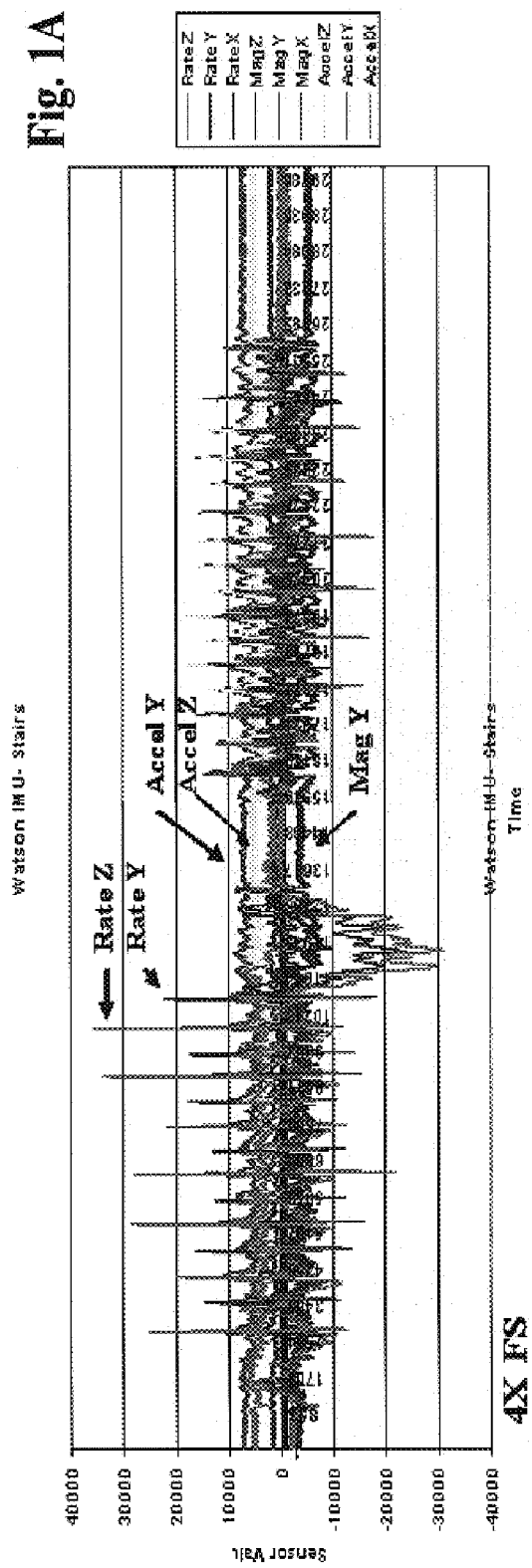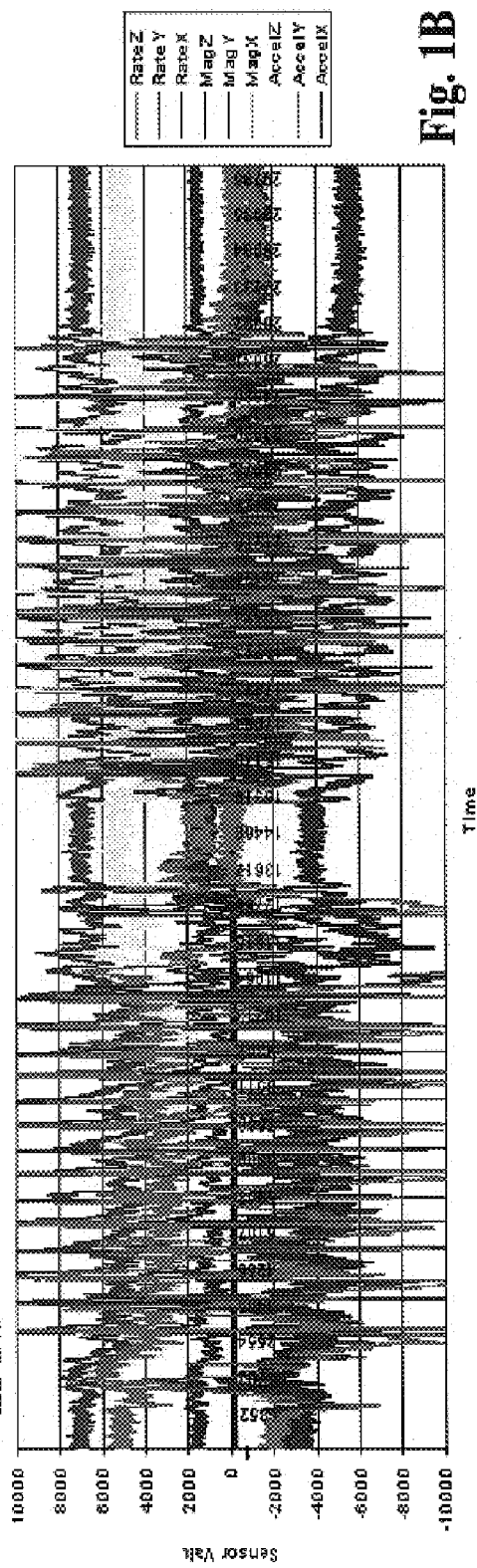

GEOLOCATION SYSTEM AND METHOD FOR DETERMINING MAMMAL LOCOMOTION MOVEMENT

CROSS-REFERENCE TO RELATED APPLICATION

The application claims the benefit under 35 U.S.C. Section 119 of provisional application No. 60/832,129, filed Jul. 21, 2006. The contents of the provisional application are incorporated herein in their entirety.

BACKGROUND AND SUMMARY

This application relates to self-locating the position of a mammal body in Earth-based coordinates, referenced to the ground, when propelled by muscular support members, and the motion of that position over time for use in navigation and health assessment.

This application describes a geolocation system for mounting on a mammal that includes simple sensing sleeves on the calves of the body support members (e.g. legs), combined with an accelerometer-based gravity direction and force sensing at the center of mass of the body. The system is connected to a digital processing unit and a battery power supply to integrate the sensing to determine kinetic and potential energy of the body locomotion over time in a method that integrates out the aperiodic motion of the body about the center of mass, and uses the residual motion to measure the center of mass locomotion from a known point. This system is placed at the mammal center of mass which, for humans, is near the small of the back.

The calf sensing includes measurement of movement in the projected Earth's magnetic field onto the cylindrical sleeve axis with interwoven magneto-resistive strips, and also measures the muscular force exerted by the calf through elastic expansion and contraction of the sleeve with interwoven, elastic-resistive strips. The system can incorporate a GPS system for continuous motion measurement, to be used for calibration of the locomotion when GPS satellite data is available, and to establish the initiation geolocation point when beginning operation in GPS-denied regions, such as in buildings, caves, and urban environments. The geolocation method combines the GPS available body movement data with the sleeve and gravity sensing data through a neural-network, nonlinear mapping function, which removes the effects of the aperiodic, nonlinear locomotion, and leaves the residual movement for determining geolocation through a Lagrangian representation of the Equations of Motion (EOM). The Lagrangian EOM is the change in the difference between the human locomotion energy of potential changes with respect to the gravitational field, and kinetic changes with respect to leg-thrust forces. This balance process of basic human navigation, sensing tilt (statocyst as gravity) and rotation (canal as angular acceleration), is measured in synchronization over time to determine locomotion center-of-mass changes in position.

The system can be embodied for many applications, such as in GPS-denied navigation for soldier training in Military Operations in Urban Terrain (MOUT), for firefighters operating in buildings, for policemen on foot operating in cities, for personnel movement in caves, and for animal location and movement monitoring, such as for domestic animals and race horses. The system can also be used in determining small changes in balance, separate from the normal locomotion, by using a GPS/INS (inertial navigation system) system to calibrate the central motion, and where the "unbalance" about-center-of-mass motion can be a precursor to subtle medical changes in older humans.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A and 1B show data collected from stair climbing.

DETAILED DESCRIPTION OF NON-LIMITING EXAMPLE EMBODIMENTS

Figure 2:
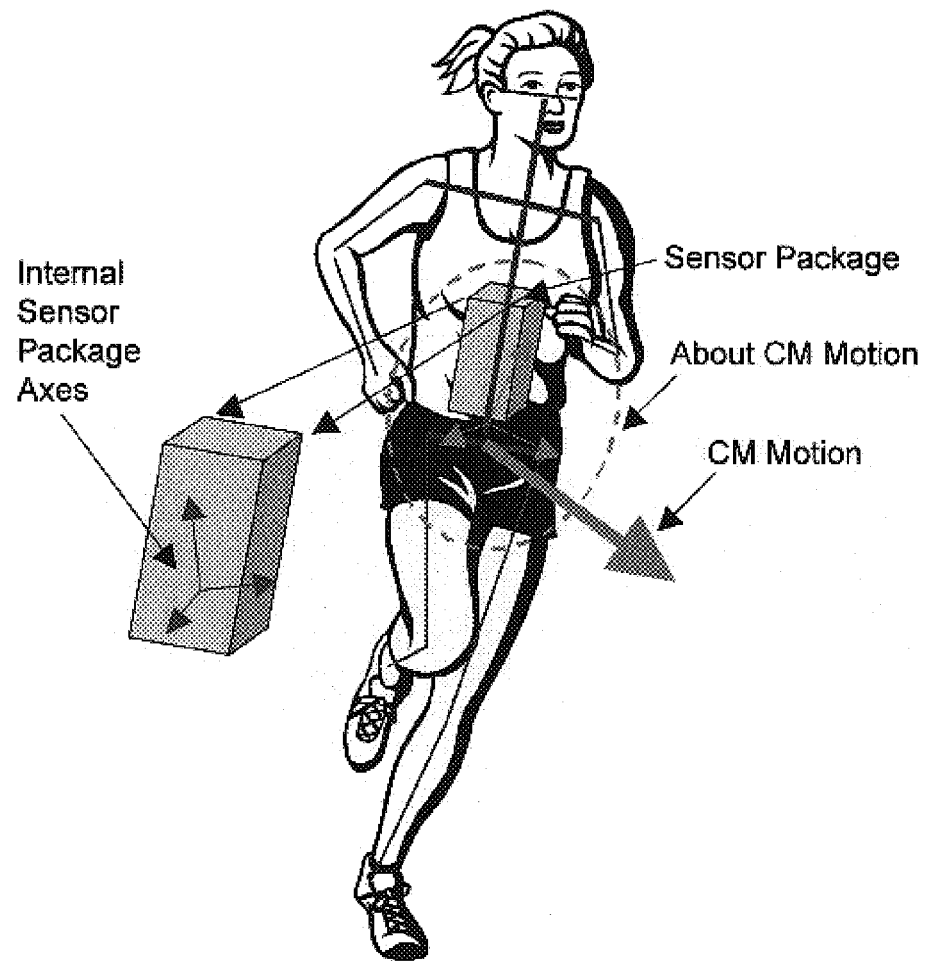
FIG. 2 shows human locomotion with sensor IMU unit axes of ACM and CM Motion.

The problem of locating position and movement of a mammal body in Earth-based coordinates is usually solved with a handheld GPS (global positioning system) navigation system, as used by humans. As is known, GPS uses a constellation satellites that transmit precise microwave signals that enable a GPS receiver to determine its location, speed and direction. In GPS-denied regions, such as in buildings, caves, and urban environments, the human must incorporate a strap down inertial measurement unit (IMU), as a system for measuring motion of the unit, collocated on the human body. A typical IMU utilizes, for example, three accelerometers and three gyros mounted to a structure which is shock isolated. The three accelerometers are used to measure linear acceleration while the gyros are used to measure angular rate.

The inventor has studied the concept of dealing with sensor measurements data from an IMU "strapped-down" to a soldier's back, with the intent of determining the location of a soldier in 3D. The IMU data showed an aperiodic motion from the oscillation of the body about the torso resulting from the process of moving the body forward in time through leg thrusts to the ground. While the motion was aperiodic, the cyclic motion appeared to return to a zero point in the oscillation. It was conjectured at that time that further study using properties of the higher-order statistics (HOS) present in the data, and possibly using neural-network data analysis, would allow for the removal of the oscillation data, and leave a residual of the general forward motion of the body.

The developments involve a formulation that allows for representing the equations of motion (EOM) in an unmanned underwater vehicle (UUV) body Lagrangian motion consisting of: a) the about center of mass (CM) motion, as water flow control surface changes in the floating water column motion from currents, etc., as an about CM (ACM) oscillation, relative to b) the CM forward motion from the dominant thrust vector of the UUV propeller water thrust. This formulation was in the inertial coordinates of the EOM, allowing for the addition of the water column motion as just an add-on motion vector to the simpler ACM/CM solution of just the UUV motion in the water. A critical point of the Lagrangian formulation was the conservation of angular momentum for no torque being present in the Euler-Lagrangian (E-L) Equations of Motion (EOM). The developments combined the neural-network (NN) formulation for adaptively solving for the Lagrangian generalized coordinate system in combination with the E-L EOM, using a GPS system to calibrate the NN solution.

Other developments involve the idea of using HOS, neural-networks, and Lagrangian EOM was extended to the application of improving soldier position location. The specific elements of this work involve the Lagrangian EOM for each soldier, being described as a "Virtual Dynamic Space Point for Collaborative Location Estimation" referred to as "VDS-3D", and allow for the improved position location through the collaborative data exchange among the soldiers, and the use of the collective soldier group motion as an additive constant similar to the water column motion in the UUV application.

Some other developments use 3-axis magnetometers (DR compass) and an accelerometer for determining forward step motion (as a silicon "pedometer") and stride motion, with on the order of 10% of distance traveled errors, and with GPS augmentation and an internal map, described in U.S. Pat. No. 5,583,776; with a 3-axis accelerometer and barometer and improvements in motion classification (see U.S. Pat. No. 6,813,582); with the addition of gyros and a blending algorithm using adaptive feedback gain and zero offset updates for improved motion state estimation (see U.S. Pat. No. 6,842, 991); Honeywell's DRM3 (dead Reckoning Module) product, described in U.S. Pat. No. 6,522,266, and now includes Point Research as a company division in Fountain Valley Calif., which contains the 9-sensors of the IMU with barometer, a motion classifier, and a Kalman filter, claiming <1% errors of distance traveled); and others (Acceleron Technologies' G-Trax product, described in U.S. Pat. Nos. 5,724,265; 5,899,963; 6,122,960; and 6,305,221 uses proprietary stride detection with neural-network approaches in capturing the cyclic motion, with subtractive corrections described as: "sensor calibration software provides the means to accurately integrate motions along each stride and to clearly identify the vertical orientation of the sensor system after each stride. In addition, for measurements outdoors, the magnetic field is used to determine the horizontal orientation of the sensor after each stride. Since the sensors are re-aligned at each stride, and the integration occurs only for the duration of a stride, errors for successive strides are statistically independent and accumulate as the square root of the number of steps, rather than as the square of time;" see "MEMS Based INS Tracking of Personnel in a GPS-denied Environment," by P. W. Kasameyer, L. Hutchings, Acceleron Technologies, LLC; M. F. Ellis, Ellis & Grant, Inc.; R. Gross, Acceleron Technologies, LLC, in ION 2004 Conference proceedings).

Further developments and extensions were made to a more useful data measurement approach from the Lagrangian EOM formulation using an entirely different sensing system, which leveraged the aperiodic nature of the human locomotion. In the course of these developments, the methods of sensing the human locomotion with limb sensing measurements of blood flow were experimentally verified using Hokanson plethysmography sensors of resistive stretch bands, that showed a measurement bandwidth in excess of 100 Hz, with a sensitivity of mild to major calf and thigh muscle force lifting of the body. Other prior approaches have used infrared and optical measurements of blood flow and blood pressure for determining stress and other muscular functions, including whole body plethysmography, with multiple frequency filters to remove artifacts in the sensor voltages not related to the body muscles contraction and blood flow.

However, none of the above-described developments incorporated, among other things, a synchronous approach for sensing both leg limbs' blood flow as a measurement of force in the Lagrangian locomotion representation, for inexpensive and self-calibrating applications in navigation and health monitoring.

Aperiodic Human Locomotion

An example aperiodic motion of the human body as measured with an IMU is shown in FIGS. 1A and 1B from a backpack on a human climbing stairs. The plot shows in FIG. 1A the IMU data collected from stair climbing. The IMU had 3 axes sensors for gyro-rate (Rate X, Rate Y, Rate Z), accelerometers (Accel X, Accel Y, Accel Z), and flux gate magnetometers (Mag X, Mag Y, Mag Z). The data has two time series groups, with the center where the climber turned around. FIG. 1B is an expansion of the vertical scale of FIG. 1A by a 4× factor to show the detail of the Mag axis changing from the rotation. The aperiodic motion is the sharp oscillations on the top half of the figure that are cyclic, but not sinusoidal. There is a half period synch delay between the two gyros, and an in-synch relationship with the accelerometers. This is the side-to-side ACM motion of the human locomotion, about the forward motion of the human body CM. The importance of these data to the Lagrangian EOM formulation is described below.

Human Locomotion

Figure 3:
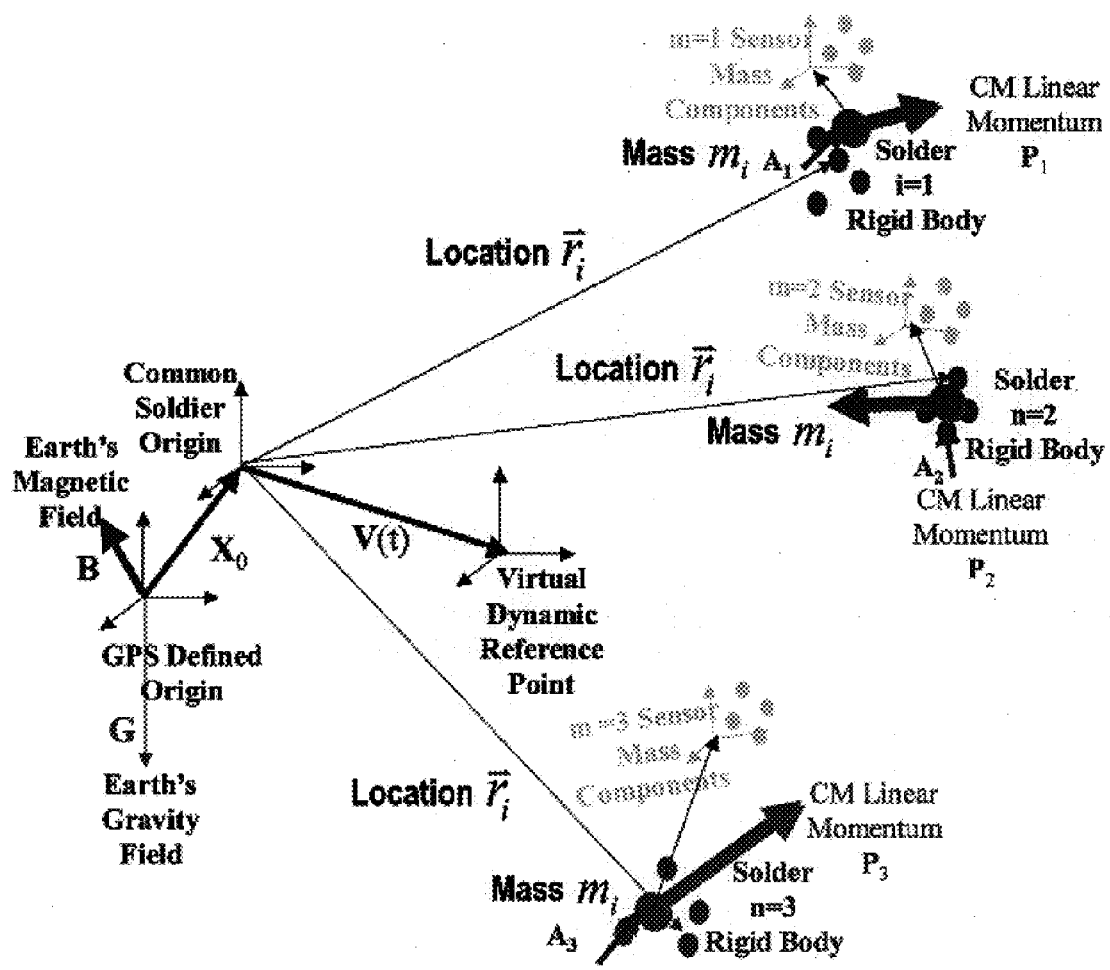
FIG. 3 shows masses and forces present in 3-Soldier and Sensor Unit Motion.

The drawing of FIG. 2 is used to explain the human locomotion process, as derived from the IMU aperiodic motion data of FIG. 1. FIG. 2 shows human locomotion with sensor IMU unit axes of ACM and CM motion. An important concept in the mass components of FIG. 2 is the manner that the forces are present on these masses, as shown in FIG. 3 for a) the forces of gravity on the IMU sensor unit masses and the human body mass components, b) the Earth's magnetic field forces on a digital compass (in the IMU) and c) the human footfall created vertical accelerations. The important points of the figure are in the individual masses of the sensor unit being separated by an unknown axes vector, due to the "non-strapped down" IMU attachment, and that the footfall force (acceleration vector $A_n$) is not in alignment with the CM motion (as a linear momentum vector, indicated in bolded letters, $P_n$), which normally is about equal to total mass of the soldier, $M_n$, aligned as $P_n=(M_n)A_n$. FIG. 3 shows masses and forces present in 3-soldier and sensor unit motion.

Human balance (see, e.g., GM Shepherd, "Neurobiology," $2^{nd}$ Ed, Oxford Press, 1988, pg 286) uses open-loop sensors of changing tilt (statocyst as velocity, v, and also gravitation, g, or as a gravireceptor, but not present in insects) and closed loop sensors of rotation from shear force motion (canal as angular acceleration ω).

Human locomotion (see ibid, pg 412) is primarily developed by exertion of thrust forces from external limbs, involving external surface contact, and muscular contractions moving the skeleton structures in the limbs (vertebrates). Locomotion is controlled by synchronized nerve firings, to execute muscular contractions, in conjunction with states of motion constraints, using closed-loop sensor feedback (e.g., walking, running, crawling, movements, resulting from the transmission of a limb pressure area in contact with the ground surface that generates the body thrust force). This is the form of an oscillating pendulum, but that is inverted, and hence has to be kept in balance. This synchronized limb movement is an aperiodic oscillation pattern of contact, which is created to conserve the angular momentum of the body's balance, during the oscillations of the upper torso, and thus the inverted-pendulum (upright human) does not fall over. Three neural components of muscle exertion and sensing feedback achieve this aperiodic, motion balance (i.e., environmental contact, effector organs with reflexive feedback, central pattern organs with spinal twist and turn feedback, and higher levels of control).

EL-EOM Solution

Figure 4:
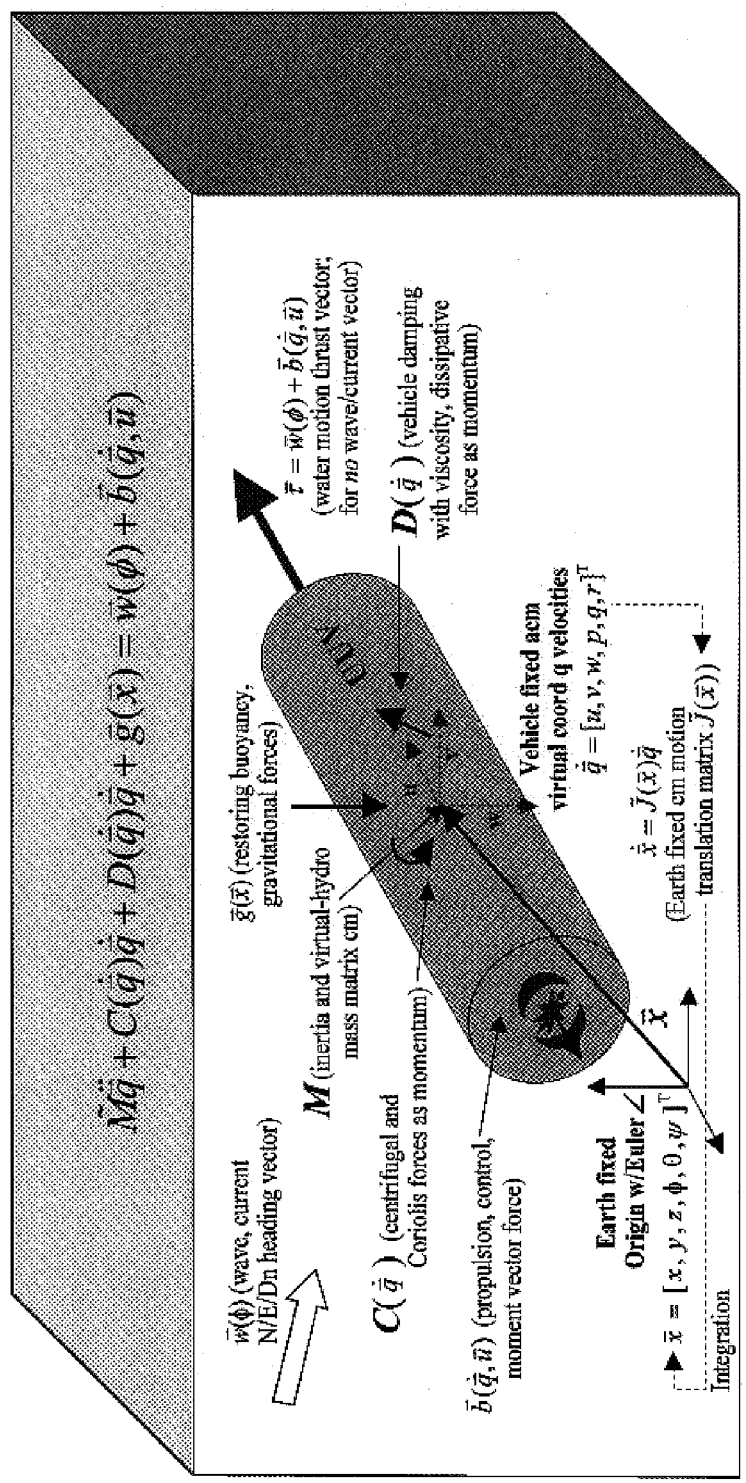
FIG. 4 shows EOM Dynamics for a UUV Moving in a Water Column.

The solution for solving for the ACM and CM dynamics of the masses in FIG. 3 is to recognize that the masses are loosely coupled together as a soldier "rigid body" (arms, legs, torso, feet, hands, head) and a sensor unit "rigid body" (IMU mass components), and that this grouping of rigid body motion (RBM) is a good approximation between the aperiodic cycle time (e.g., the locomotion steps driving the inverted pendulum). First, the analogy used in the Euler-Lagrange EOM (EL-EOM) in FIG. 4, for the referenced UUV motion, will be described, and then the EL-EOM will be described in the generalized coordinates of the Lagrangian formulation, and related back to the physical coordinate system. The UUV motion is shown in FIG. 4, with the Newtonian Second Law, is as an "F=MA" formulation at the top of the figure. This is the EOM dynamics for a UUV moving in a water column.

The equation at the top of FIG. 4 has the F=ma Newtonian form in the generalized coordinates (q), and a collection of the following forces and moments:

1. M UUV mass moment matrix of inertia and hydro effective masses (strictly the body inertia and the combined sensor unit inertia; neglected to be small as well as other soldier pack inertias)
2. C for the centrifugal and Coriolis forces as momentum (insignificant with respect to the small, slow velocity changes over time and short spatial extents)
3. D for the vehicle damping matrix with viscosity of the water as a dissipative force momentum ($F_d$, negligible for body motion in air, but includes the sliding of the footfalls)
4. g for the restoring buoyancy of gravity (for the soldier, this is a falling force, with the buoyancy of the legs keeping the height constant above the ground by the legs, under the rigid body assumption between aperiodic cycles.
5. w for the wave, current water motion heading vector as an additive velocity (for the soldier, this is a constant motion over the ground at a constant height, as an additive velocity)
6. b for the UUV propulsion and moment control vector from the thrusting of the propeller and fins (here it is just what is provided to the soldier from the footfalls).

The translation from the coordinates of FIG. 3 of the masses, shown in FIG. 4 from the ACM coordinates (x) to the CM coordinates (X) for position location is not the desired path; rather the problem in the ACM coordinates is solved using Euler angles and a Lagrangian formulation. The UUV Lagrangian form is formed for "rigid body" motion in generalized coordinate space q, in place of the normal F=ma formulation (e.g., Newton's Second Law of Motion).

These generalized coordinates are not in any of the coordinates shown in FIG. 3 (e.g., the CM motion defined from the origin at $X=[x, y, z, \phi, \theta, \psi]^T$ for each mass, but has the ACM motion from Euler Equations in the inertial coordinates in velocity units as $dq/dt=[u, V, W, p, q, r]^T$, where for the generalized coordinate representation for X is now in generalized coordinates for each of the masses in FIG. 3, as $r=r(q_i, q_j, q_k, t)$. But, because it is an inertial coordinate system, it has the property of Newton's First Law and Third Laws (i.e., for velocity v, with linear momentum p=mv, for an additive velocity V, leaves the velocity sum as v', unchanged (v=dr/dt)). This means that an added velocity of the soldier motion is unchanged to the ACM dynamics, indicating conservation of total linear momentum (e.g., motion of surge forward momentum, Mu, for the u axis, sway or slip sideways momentum, Mv, for the v axis, and up/down heave momentum, Mw, for the w axis), which is similar to rigid body movement, where the sum of time derivatives of the linear momentums is equal to the force on each mass.

The Lagrangian, L, uses the static potential energy V (whose vector gradient is the negative of the vector force, e.g., the integrated force of potential energy gradient for work, becomes a generalized force), and is subtracted from the kinetic energy T (i.e., ½ the momentum dot product with the time derivative of the generalized coordinate, as T=½(p·dq/dt); i.e., where L=T−V). The Hamiltonian conservation of energy (E, for E=T+V) is based on a stationary action trajectory, where a dynamic angular momentum in ACM motion is the Euler moment of force, as torque N (N=r×F=dL/dt, for angular momentum L=r×p). In a zero torque condition arising from closed loop feedback, angular momentum is conserved (L=constant, with motion of roll rate (p=dφ/dt), pitch rate (q=dθ/dt), and yaw or heading rate (r=dψ/dt)).

This is conserved angular momentum over the aperiodic cycle is like a gravity driven swing or pendulum, where the motion in gravity changes between all kinetic energy (KE=T) maximums at the swing-cycle bottom, and the swing-cycle tops of all potential energy (PE=V). This PE/KE change in the human locomotion is an inverted pendulum oscillation as essentially the aperiodic cyclic motion of the human body model in a generalized coordinate for ACM. The CM motion has an inertia moment, and an angular velocity, while the ACM motion has the aperiodic angular momentum velocity.

The F=ma EOM now becomes under these pseudo-RBM assumptions the following Second Order EL-EOM (L2) shown below for the generalized force components, $Q_i$.

$$L2)\ \text{Generalized Coordinates Force} \quad Q_1 = \frac{d}{dt}\frac{\partial T}{\partial \dot{q}_i} - \frac{\partial T}{\partial q_i}$$

$$\text{in Generalized Coordinates} \quad \vec{r} = \vec{r}(q_i, q_j, q_k, t)$$

$$\text{For Kinetic Energy} \quad T = \frac{1}{2}\sum_i p_i \dot{q}_i$$

The Third Order EL-EOM is shown below with the definition of the Lagrangian, L, in terms of the KE and PE terms in the generalized coordinates.

$$L3)\ \text{Lagrange Force} \quad \frac{d}{dt}\frac{\partial T}{\partial \dot{q}_i} - \frac{\partial L}{\partial q_i} = 0$$

$$\text{Lagrangian} \quad L = T - V$$

$$\text{Static Potential} \quad V = V(\vec{r}(\vec{q}, t))$$

By combining the dissipative forces into the thrust vector, T, one now has the EOM for the human body in generalized vector coordinates as:

$$\vec{\tau} = \frac{d}{dt}\left(\frac{\partial T}{\partial \dot{\vec{q}}}\right) - \frac{\partial T}{\partial \vec{q}}$$

Here, the Euler-Lagrangian EOM is just the "thrust" on the ACM motion, τ, related to the time derivatives of the kinetic energy in the ACM, relative to the time derivative velocity of the generalized coordinate (dq/dt), and the coordinate itself, q, as shown below. This is because of the dependence of position dependent energy on the generalized coordinates. There is an approximation in ignoring small terms in this from the "F=ma" formulation; the approximations are a) the damping of motion through the air and shoe slip is minimal, b) the gravitational forces on all of the clique masses are almost the same, due to a similar altitude, c) all of the inertial moments are in the total body mass, and d) centrifugal and Coriolis forces are in the momentum. This leaves just the kinetic energy with a dissipative force from the shoe slip, as described next in a human locomotion model.

Human Locomotion Model

Figure 5:
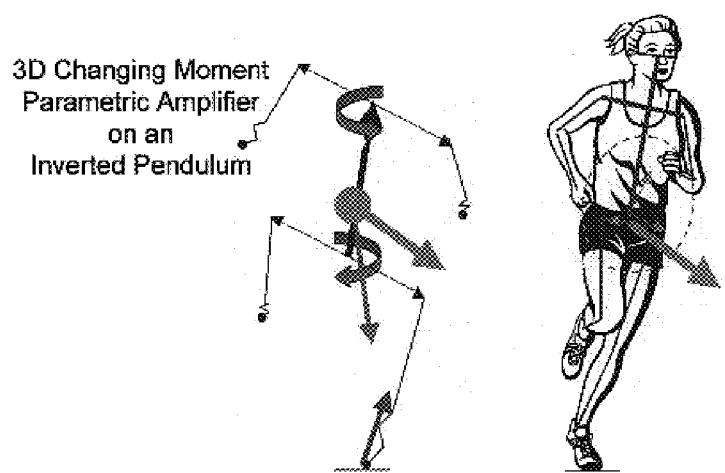
FIG. 5 shows a human locomotion model dynamic as a parametric amplifier.

While there have been many human locomotion models for various applications, a recent model (see R. Allendorfer, D E Koditschek, P Holmes "Towards a factored analysis of legged locomotion models," IEEE proceedings Int. Conf Robotics & Automation, Taipei, Taiwan (Sep. 14-19, 2003)) uses the form of leg swing as the inverted pendulum, and foot slip for self stability. One critical assumption in this approach is to show the conservation of torque in the human locomotion by the arms and legs, for a constant linear CM movement (i.e., aperiodic, but still cyclic to a zero point oscillation). This new human locomotion modeling has added new modeling to this component of the simulation, e.g. leg swing and self-stability. FIG. 5 illustrates this motion, with the dynamic example of FIG. 2, where the human locomotion is modeled as a dynamic parametric amplifier.

The motion of the runner is simplified on the left side as "rigid body" motion of the spine twisting, the arms and legs "pumping, and the side-to-side rocking of the body from the changing leg forces from the footfalls. Because this motion is about the vertical gravity vector shown as a green arrow in the figure, it is considered as the motion of an inverted pendulum. Also, because it is similar to the cyclic motion of the swing dynamics changing from KE to PE to KE, it can also be considered as a parametric amplifier with the length of the arm or leg being the changing parameter of the nonlinear amplification dynamic (e.g., the swing pumping is in phase with the all PE point of the cycle). This is a mass movement parametric amplification, only here, the runner in the figure is changing the mass positions in phase with the torso twisting, which is in phase with the footfalls.

In accordance with the techniques described herein, the assumptions for solving the soldier navigation from a Lagrangian formulation, and for modeling the human locomotion as that of a parametric amplifier in synch with changing footfalls is valid under the conditions of a) the pseudo-RBM condition is to be constant over the aperiodic cycle, and b) linear and angular momentum are conserved, when ignoring the constant velocity of the CM motion in the Lagrangian formulation. The assumptions needed for the parametric amplifier are contained in the ACM motion represented in the generalized coordinate space, which is dynamically consistent with the inertial motion. Solving for this coordinate space for an individual may, for example, be part of a customization of the sensor package and human motion using GPS to determine these parameters that map the ACM motion into the CM coordinates (see FIG. 4).

Developing prototype systems in this environment depends dramatically on the application. However, a simplification of the problem is possible if the IMU sensor package is replaced with a much simpler design, building on the need only for knowledge of the two vector forces affecting the Newtonian motion of the body, as computed in the Lagrangian formulation. The only two forces are a) the force of gravity (G, in the figure from g used previously, in green), and b) the force of the footfall (A in magenta), as shown in FIG. 3. The motion of FIG. 5 is then the transfer of energy between kinetic and potential within the Lagrangian representation, and over the aperiodic period of hips and shoulders swinging, because of being pumped by arm motion and footfalls in the parametric amplification, the angular momentum is conserved. Hence, the only required measurement is for a 3-axis accelerometer package to determine the gravitational force as a tilt, and a force-measuring device placed on the major muscles of the legs to measure the footfall force (e.g., an expansive-contractive, resistive monitoring sleeve wrapped on the calf of each leg). An additional requirement is to determine the rotational forces from the residual angular momentum of the aperiodic motion arising from the angular acceleration, which will be accounting for the CM motion (the orange vector of FIG. 5), and can be used for human location. This measurement can be made by including a magneto resistive set of vertical bands in the leg sleeve, which will sense rotational motion within the earth's magnetic field (B in brown of FIG. 3).

Figure 6:
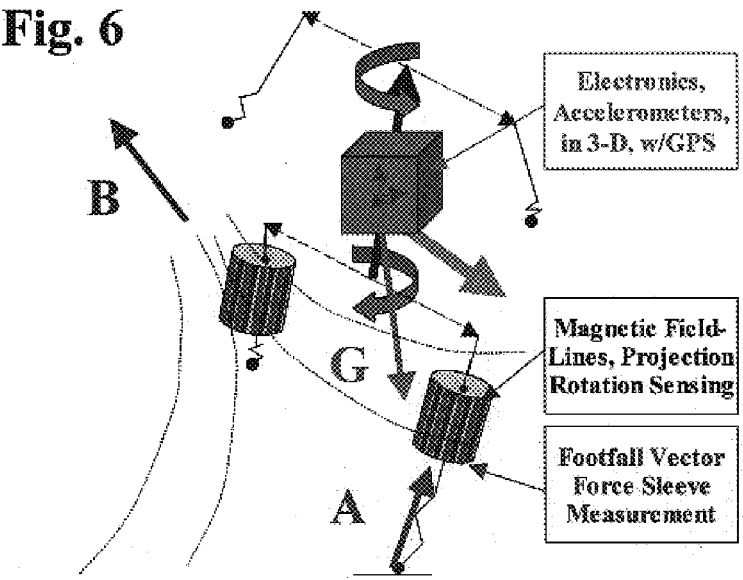
FIG. 6 shows an example sensing design for E-L human locomotion measurements.

FIG. 6 shows the instrumentation for this measurement added to the vector motion of FIG. 5. An example sensing design is for an E-L human location measurement. The two calf sensing sleeves have the resistive expansion strips shown in magenta, for measuring A, and the magnetic sensing strips shown in brown for measuring B. Also shown, is the 3-axis accelerometer package (blue vectors) shown in green for measuring G, with an additional component of a miniature GPS package used for locating the human motion during neural-network mapping. The system is able to train when GPS is available, and then augment location and motion sensing with the E-L formulation of just the two force vector measurements, and the rotational component of the body motion, as sensed in the calf sleeve.

Figure 7:
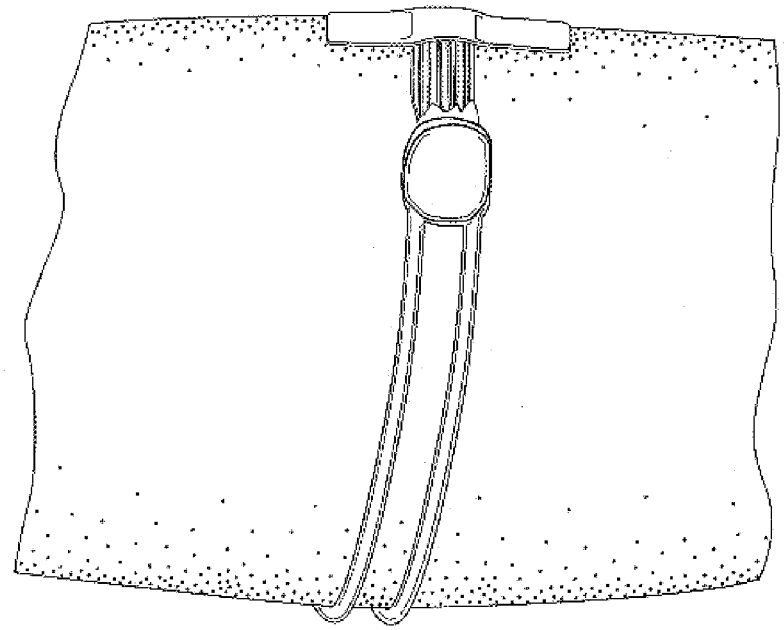
FIG. 7 shows example plethysmograph conductive sensors for force and blood flow measurements.
Figure 8:
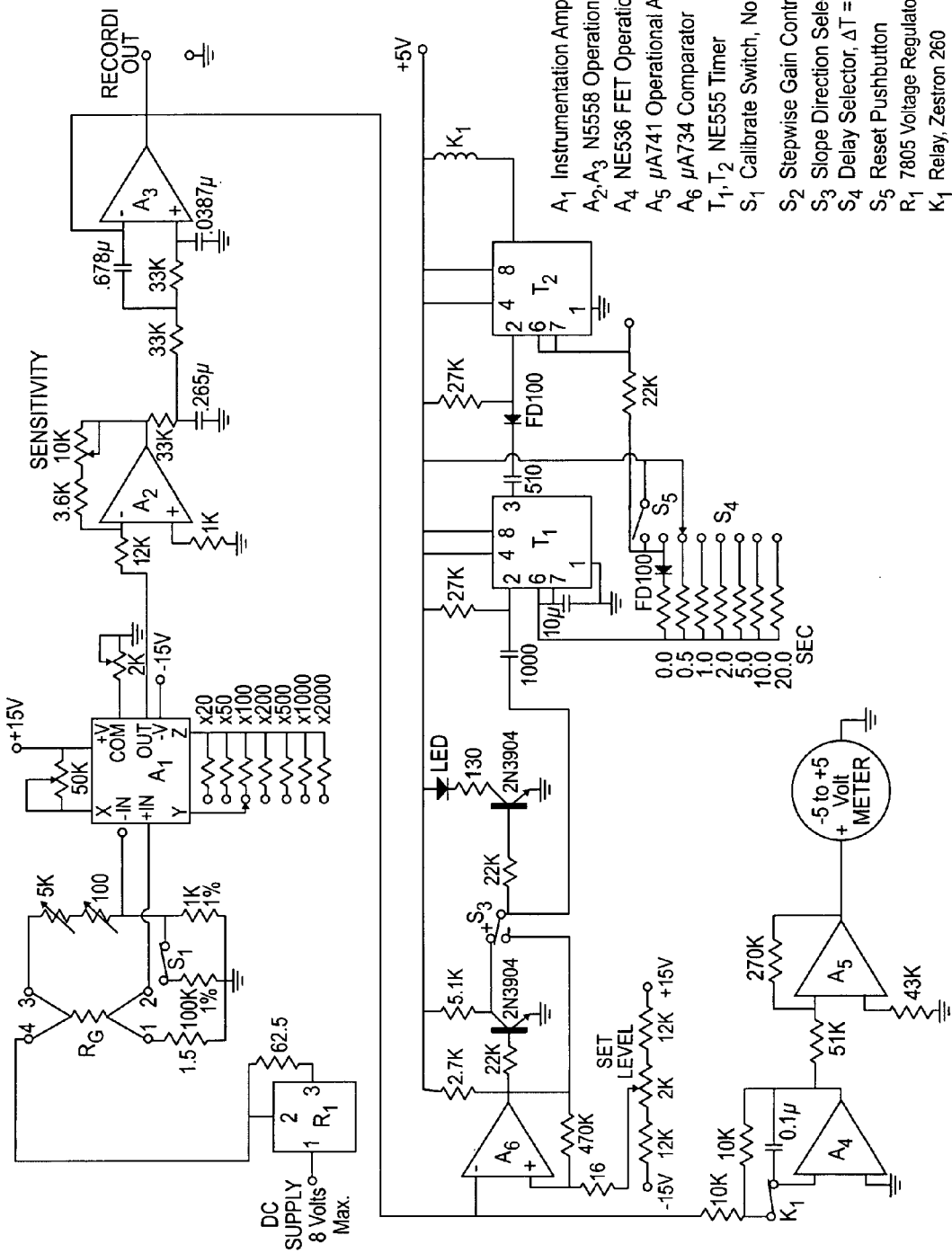
FIG. 8 shows a four wire bridge circuit for conductive sensor readouts.
Figure 9:
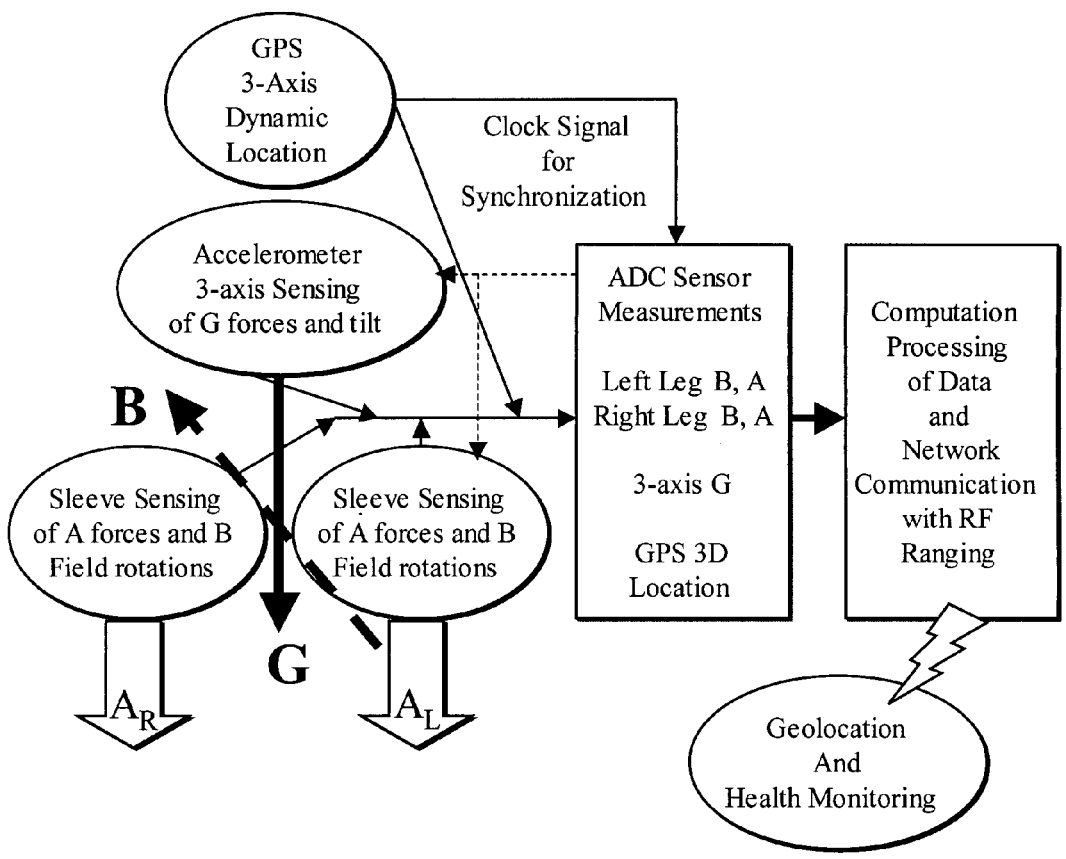
FIG. 9 shows a two sleeve system diagram for locomotion and health applications.

FIG. 7 shows example plethysmograph conductive sensors for force and blood flow measurement and FIG. 8 shows a four-lead bridge circuit for conductive sensor readouts. The actual circuit embodied in the system described herein uses a high frequency driving circuit to remove DC effects, and move the measurement frequency band to a frequency out of interference bands. A down conversion, mixer circuit is filtered into a digital sampling circuit to form in a computational processor, instantaneous measurements of the Lagrangian, and integrated measurements that track the aperiodic oscillations for angular momentum estimation feedback. FIG. 9 shows a system of two sleeve sensors measuring both muscle force and rotation, with a neural-network algorithm mapping the sensor measurements into the EL-EOM formulation from previous calibration in GPS accessed environments.

The systems and methods described above provide a geolocation system for mounting on a mammal that includes simple sensing sleeves on the calves of the body support members, combined with an accelerometer based gravity direction and force sensing at the center of mass of the body. The system is connected to a digital processing unit and battery power supply to integrate the sensing to determine kinetic and potential energy of the body locomotion over time in a method that integrates out the aperiodic motion of the body about the center of mass, and uses the residual motion to measure the center of mass locomotion from a known point. This system is placed at the mammal center of mass which, for humans, is near the small of the back.

The calf sensing includes measurement of movement in the projected Earth's magnetic field onto the cylindrical sleeve axis with interwoven magneto-resistive strips, and also measures the muscular force exerted by the calf through elastic expansion and contraction of the sleeve with interwoven, elastic-resistive strips. The system incorporates a GPS system for continuous motion measurement, to be used for calibration of the locomotion when GPS satellite data is available, and to establish the initiation geolocation point when beginning operation in GPS-denied regions, such as in buildings, caves, and urban environments. The geolocation method combines the GPS available body movement data with the sleeve and gravity sensing data through a neural-network, nonlinear mapping function, which removes the effects of the aperiodic, nonlinear locomotion, and leaves the residual movement for determining geolocation through a Lagrangian representation of the Equations of Motion (EOM). The Lagrangian EOM is the change in the difference between the human locomotion energy of potential changes with respect to the gravitational field, and kinetic changes with respect to leg-thrust forces. This balance process of basic human navigation, sensing tilt (statocyst as gravity) and rotation (canal as angular acceleration), is measured in synchronization over time to determine locomotion center-of-mass changes in position.

The system can be embodied for many applications, such as in GPS-denied navigation for soldier training in Military Operations in Urban Terrain (MOUT), for firefighters operating in buildings, for policemen on foot operating in cities, for personnel movement in caves, and for animal location and movement monitoring, such as for domestic animals and race horses. The system can also be used in determining small changes in balance, separate from the normal locomotion, by using a GPS/INS system to calibrate the central motion, and where the "unbalance" about-center-of-mass motion can be a precursor to subtle medical changes in older humans.

Features described in this application include:

- A method for combining force vector motion sensors of mammal support member thrusting to accomplish position and motion prediction of the mass center.
- The use of calf muscle sensors in the aforementioned method.
- The incorporation of magneto-resistive strips woven into the calf sensor.
- The incorporation of elastic-resistive strips woven into the calf sensor.
- The incorporation of accelerometer sensors placed at the mass center of the mammal for determining the gravitational vector force.
- A method of calibrating during GPS sensed motion of the mammal, a neural-network algorithmic approach to nonlinearly map the sensor data into the GPS sensed motion in the E-L formulation.
- The representation of the mammal EOM using a Lagrangian mathematical formulation of kinetic and potential energies that allows for removal of the aperiodic mammal locomotion sensing through integration time to a zero angular momentum.
- The use of neural-network modeled mammal locomotion for determining the motion state in choosing the proper integration time.
- The use of the sensor balance determination with GPS calibration as a subtle health monitoring system for sensing precursor conditions in normal walking activities of elderly humans.
- The use of the balance determination and changes in monitoring the health of other mammals, including race horses, and human athletes.

Documents describing IMUs and related subject matter include:

U.S. Pat. No. 5,583,776
U.S. Pat. No. 5,724,265
U.S. Pat. No. 5,899,963
U.S. Pat. No. 6,122,960
U.S. Pat. No. 6,292,106
U.S. Pat. No. 6,305,221
U.S. Pat. No. 6,522,266
U.S. Pat. No. 6,579,097
U.S. Pat. No. 6,608,589
U.S. Pat. No. 6,813,582
U.S. Pat. No. 6,842,991
U.S. Pat. No. 6,859,170

T I Fossen, S I Sagatum, "Lagrange Formulation of Underwater Vehicles," ISSN #0-7803-0233 (8/91), pg 1029.

P W Kasameyer, L Hutchings, "MEMS Based INS Tracking of Personnel in a GPS-denied Environment," Acceleron Technologies, LLC; M. F. Ellis, Ellis & Grant, Inc.; R. Gross, Acceleron Technologies, LLC, in ION 2004 Conference proceedings.

R Allendorfer, D E Koditschek, P Holmes, "Towards a factored analysis of legged locomotion models," IEEE proceedings Int. Conf Robotics & Automation, Taipei, Taiwan (Sep. 14-19, 2003).

M D Goldman, H J Smith, W T Ulmer, "Whole-body plethysmography," Chpt. 2, ERS Journals Ltd, UK, Eur Respir Mon, 31, pg. 15-43 (2005).

A Urso, R Shankar, B Szabo, "Design of a High Signal to Ratio Electrical Impedance Plethysmography," Proceed SouthEastcom, 1999 Session 11F5, pg 1100-1104 (2005).

D E Hokanson, D S Sumner, D E Stirandness, "An Electrically Calibrated Plethysmograph for Direct Measurement of Limb Blood Flow," IEEE Trans Bio Eng BME22 (1), pg 25-29 (January 1975).

P J Pretorius, N T Malan, H W Huisman, P Laubscher, F C Eloff, F A J de Klerk, and S J van der Herwe, "The Use of a Continuous Non-Invasive Blood Pressure Recorder to Study Experimental Stressors," Noninvasive Cardiovascular DJTUI-CS, IEEE Eng in Med C Bio Society 11th Annual Intl Conf #CH2770-6/89/0000-0128, pg 0128-0129 (1989).

K Ikeda, Y Kusaka, "Improvement of Photo-electric Plethysmograph Applying Newly Developed Opto-electric Devices," 1999 IEEE TENCON, Conf#0-7803-5739, pg 1109-1112 (1999).

J Rosell, K P Cohen, J G Webster, "Reduction of Motion Artifacts Using a Two-Frequency Impedance Plethysmograph and Adaptive Filtering," IEEE Trans Bio Med Eng 42, (10), pg 1044-1048 (October 1995).

J Wtorek, A Poliriski, "Multi-frequency Impedance Plethysmograph," IEEE Instrument and Measurement Technology Conference, Brussels, Belgium, June 4-6, pg 1452-1455 (1996).

The contents of each of these documents is incorporated herein in its entirety. The identification of these documents does not constitute an admission that the information contained therein is prior art to the subject patent application.

While the systems and methods have been described in connection with what is presently considered to practical and preferred embodiments, it is to be understood that these systems and methods are not limited to the disclosed embodiments.

I claim:

1. A geolocation system for mounting on a mammal, comprising:
   muscular force sensors for measuring muscular force exerted by support members of the mammal;
   movement sensors for sensing movement in the Earth's magnetic field;
   gravity sensors for sensing gravity forces at the center of mass of the body of the mammal; and
   a processing system for using outputs of the muscular force sensors, the movement sensors and the gravity sensors to determine movement of the mammal.

2. The system according to claim 1, wherein the muscular force sensors comprise calf muscle sensors provided as sleeves including interwoven, elastic-resistive strips.

3. The system according to claim 2, wherein the movement sensors comprise magneto-resistive strips in the sleeves.

4. The system according to claim 1, wherein the force sensors comprise accelerometers disposed at the mass center of the mammal.

* * * * *